(12) United States Patent
Ribeiro et al.

(10) Patent No.: US 12,318,395 B2
(45) Date of Patent: Jun. 3, 2025

(54) ETHINYL ESTRADIOL-β-CYCLODEXTRIN COMPLEX AND PROCESS FOR PREPARING THEREOF

(71) Applicant: LABORATORIOS LEON FARMA, S.A., Villaquilambre (ES)

(72) Inventors: Andreza María Ribeiro, Villaquilambre (ES); María Dolores Moya Ortega, Villaquilambre (ES)

(73) Assignee: LABORATORIOS LEON FARMA, S.A., Villaquilambre (ES)

( * ) Notice: Subject to any disclaimer, the term of this patent is extended or adjusted under 35 U.S.C. 154(b) by 971 days.

(21) Appl. No.: 17/413,692

(22) PCT Filed: Dec. 11, 2019

(86) PCT No.: PCT/EP2019/084591
§ 371 (c)(1),
(2) Date: Jun. 14, 2021

(87) PCT Pub. No.: WO2020/120548
PCT Pub. Date: Jun. 18, 2020

(65) Prior Publication Data
US 2022/0040200 A1    Feb. 10, 2022

(30) Foreign Application Priority Data
Dec. 13, 2018 (EP) ..................... 18382921

(51) Int. Cl.
*A61K 31/565*    (2006.01)
*A61K 31/519*    (2006.01)
*A61K 47/69*    (2017.01)

(52) U.S. Cl.
CPC .......... *A61K 31/565* (2013.01); *A61K 31/519* (2013.01); *A61K 47/6951* (2017.08)

(58) Field of Classification Search
CPC . A61K 31/565; A61K 31/519; A61K 47/6951
See application file for complete search history.

(56) References Cited

U.S. PATENT DOCUMENTS

| 4,727,064 A | * | 2/1988 | Pitha | ................... C08B 37/0012 |
| | | | | 106/205.01 |
| 5,798,338 A | * | 8/1998 | Backensfeld | ........ A61K 31/567 |
| | | | | 514/182 |
| 2017/0368197 A1 | | 12/2017 | Keltjens et al. | |

FOREIGN PATENT DOCUMENTS

| EP | 1 044 975 A | 10/2000 |
| EP | 1 353 700 | 10/2003 |
| EP | 3 666 260 A1 | 6/2020 |

(Continued)

OTHER PUBLICATIONS

Blode et al., Contraception 77 (2008) 171-176 (Year: 2008).*

(Continued)

*Primary Examiner* — San Ming R Hui
(74) *Attorney, Agent, or Firm* — Jenkins, Taylor & Hunt, P.A.

(57) ABSTRACT

The process comprises combining prepared β-cyclodextrin solution and prepared ethinyl estradiol solution, then removing the solvent by spray-drying for obtaining an ethinyl estradiol β-cyclodextrin complex. The obtainable amorphous ethinyl estradiol β-cyclodextrin complex is suitable for use in pharmaceutical compositions and formulations comprising it.

18 Claims, 8 Drawing Sheets

(56) References Cited

FOREIGN PATENT DOCUMENTS

| ES | 2850278 B2 | 8/2021 |
|----|------------|--------|
| JP | 2004-518656 A | 6/2004 |
| JP | 2015-536353 A | 12/2015 |
| JP | 2022-513237 A | 2/2022 |
| WO | WO 2000/037109 | 6/2000 |
| WO | WO 2002/49675 | 6/2002 |
| WO | WO 2014/146975 A1 | 9/2014 |

OTHER PUBLICATIONS

International Search Report corresponding to International Application No. PCT/EP2019/084591 dated Jun. 18, 2020.
Written Opinion corresponding to International Application No. PCT/EP2019/084591 dated Jun. 18, 2020.
International Preliminary Report on Patentability corresponding to International Application No. PCT/EP2019/084591 dated Jun. 24, 2021.
King, C. J., (1987). Spray Drying Handbook, Fourth Edition by K. Masters, Halstead Press, New York, 1985, 696 pp. AlChE Journal, vol. 33, No. 1, Jan. 1987, pp. 172-173.
Notice of Reasons for Refusal corresponding to Japanese Application No. 2021-534321 dated Dec. 12, 2023.

\* cited by examiner

FIGURE 1.1
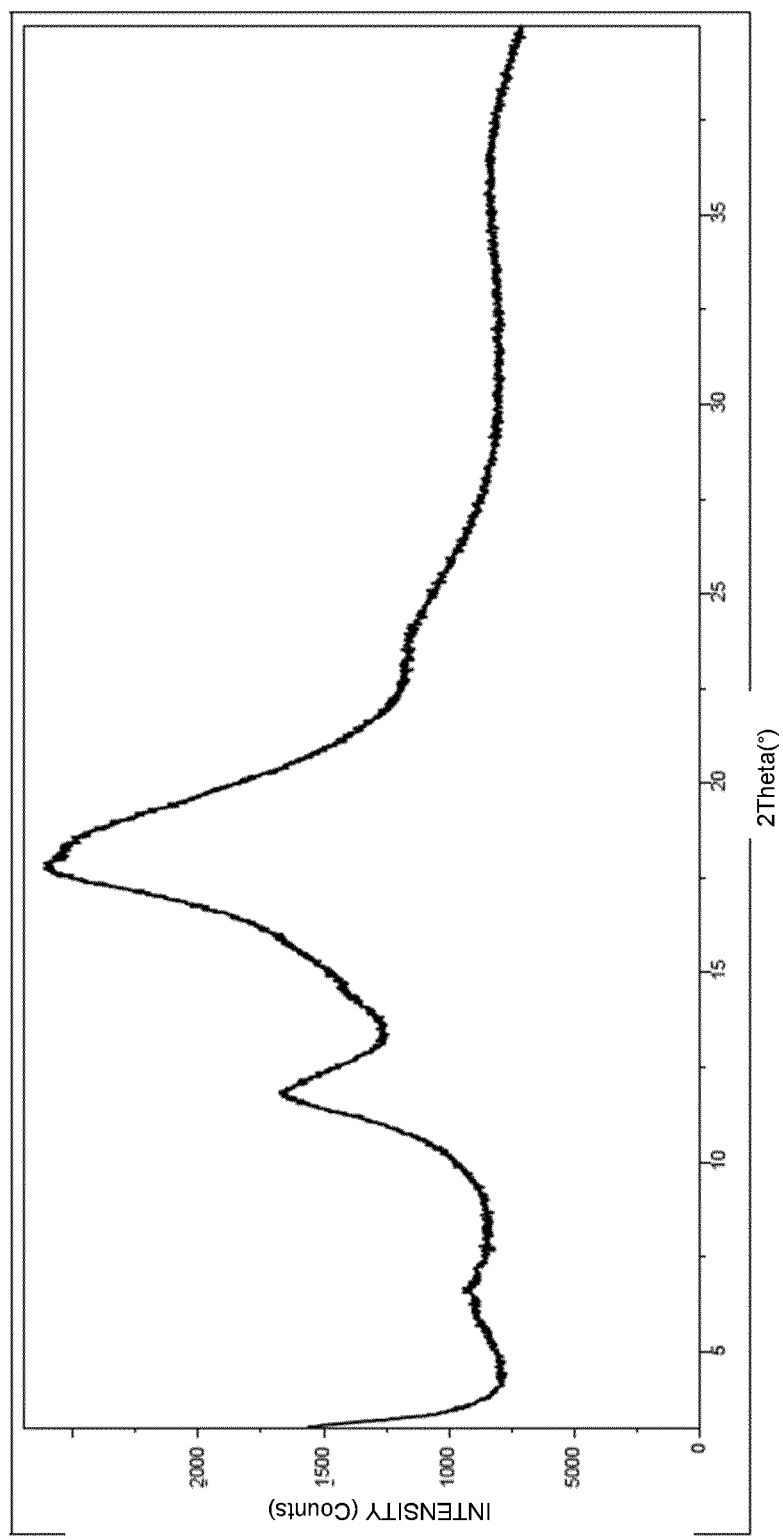

FIGURE 1.2
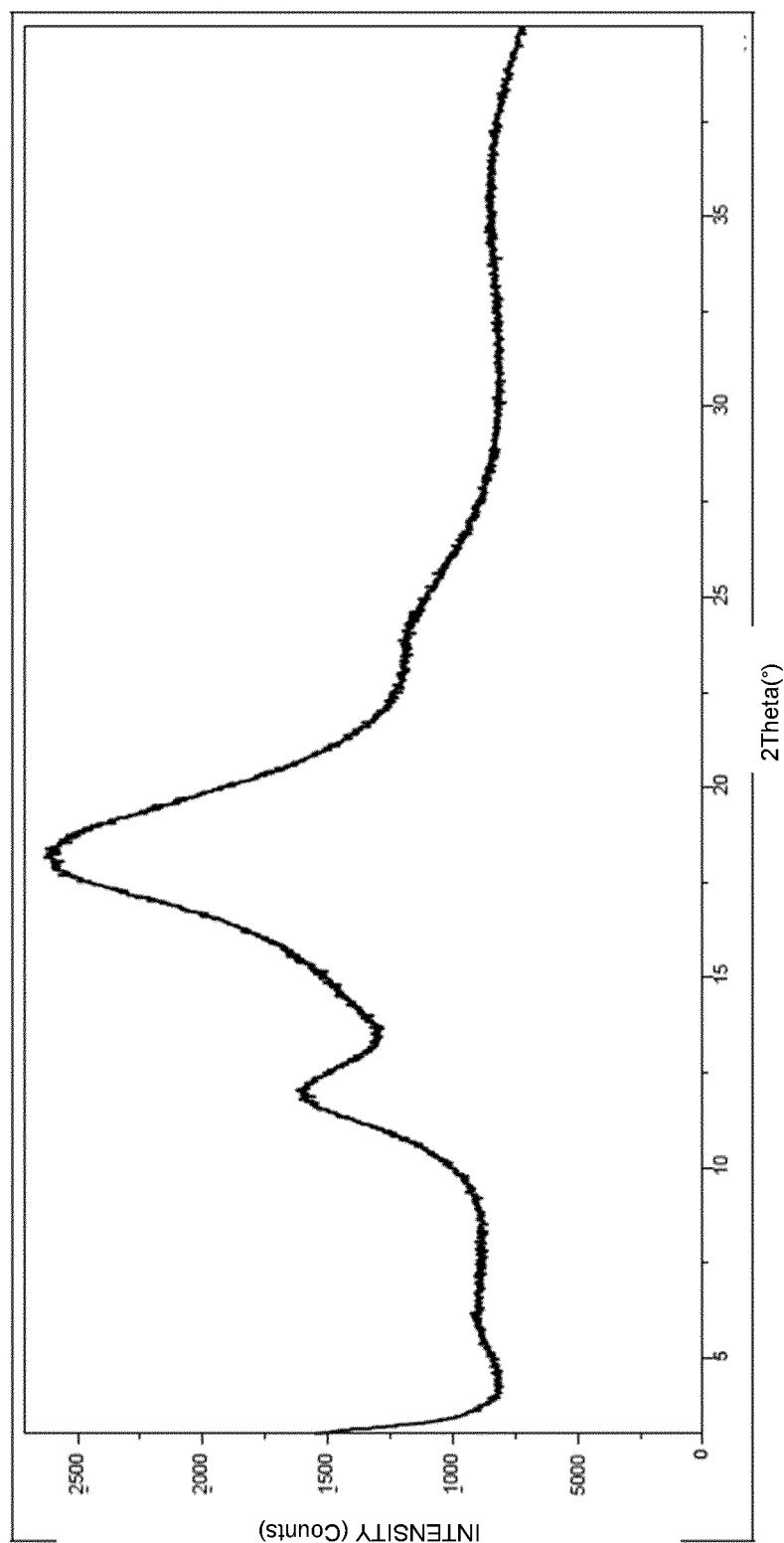

FIGURE 4.1
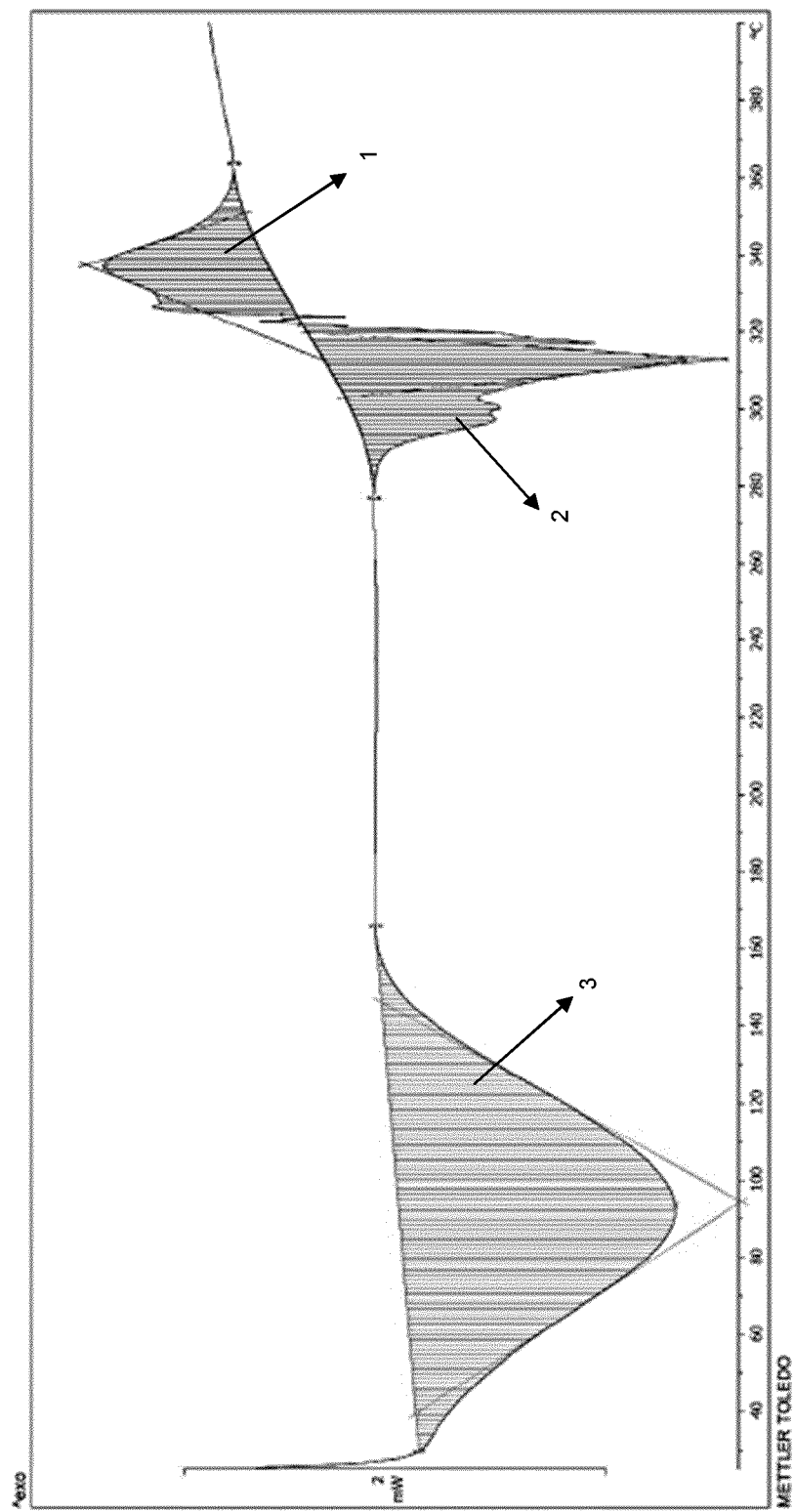

FIGURE 4.2
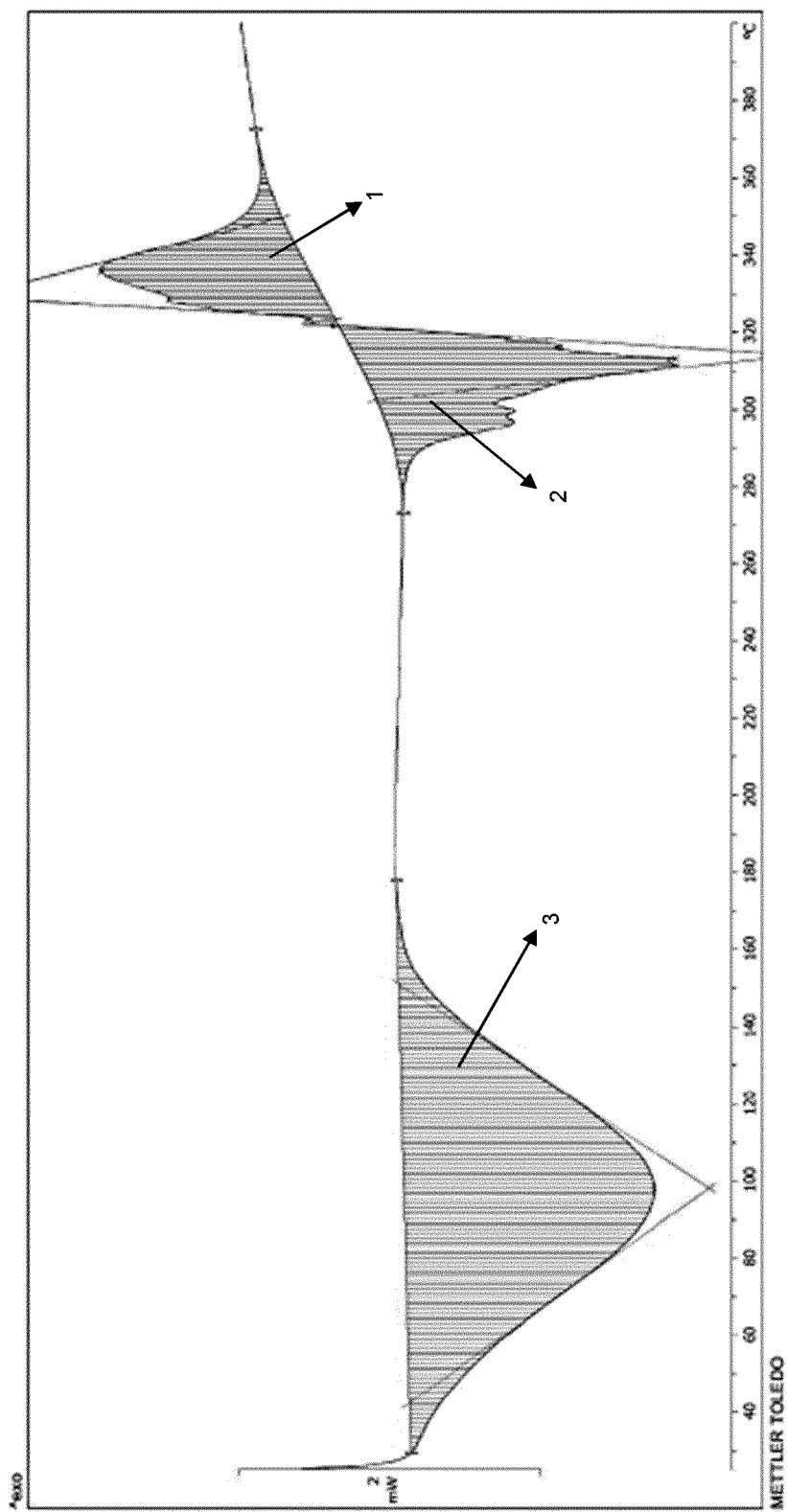

ETHINYL ESTRADIOL-β-CYCLODEXTRIN COMPLEX AND PROCESS FOR PREPARING THEREOF

FIELD OF THE INVENTION

The present invention relates to a new process for the manufacture of an ethinyl estradiol β-cyclodextrin complex as well as to an amorphous ethinyl estradiol β-cyclodextrin complex obtainable by this process, and pharmaceutical compositions and formulations comprising it.

BACKGROUND OF THE INVENTION

Cyclodextrins (CDs) are cyclic oligosaccharides obtained from starch by enzymatic cyclisation using enzymes called cycloglycosyl transferases. There are several unsubstituted cyclodextrins, the most commonly known being the α-cyclodextrin (6-cyclo-α-(1,4)-anhydroglucose units, β-cyclodextrin (7-cyclo-α(1,4)-anhydroglucose units) or γ-cyclodextrin (8 cyclo-α(1,4)-anhydroglucose units). However so far only β-cyclodextrin and its derivatives has a significant industrial usage in the pharmaceutical field.

The use of cyclodextrins as complexing agents for materials is known. Cyclodextrins complexes are particularly desirable when the active is an estrogen. Cyclodextrin complexes provide stable, standardized powders containing the active that are easy to use. Being a powder, the cyclodextrin complexes are easy to measure, handle, and store.

Ethinyl estradiol is a synthetic estrogen widely used in combination with different progestagens in various oral hormonal contraceptives, including emergency and postcoital contraceptives, and hormone replacement therapy (HRT).

Pharmaceutical products comprising ethinyl estradiol often consist of low dosages of active ingredient required per single dosage, often ranging between 10 μg and 50 μg, and then, it is problematic to manufacture unit dosage formulations with reliably consistent amounts of active agent, which do not fluctuate within one batch or between batches.

The stability and solubility of ethinyl estradiol in the above-mentioned products is one of the most critical issues in the production of these products. By complexing the estrogen with a cyclodextrin the estrogen is protected from degradation because of reactions induced by heat, light, and/or reaction with oxygen or other compounds and provides a complex that is stable for a longer period of time. Because of the improved stability measuring amounts of the estrogen is more precise since its content remains more constant over time.

U.S. Pat. No. 5,798,338 discloses that the oxidative degradation of 17-α-ethinyl estradiol is reduced upon forming clathrates (complexes) between β-cyclodextrin and 17-α-ethinyl estradiol. The complexes are obtained by co-precipitation of ethinyl estradiol and the β-cyclodextrin from a water or a water-ethanol solution.

U.S. Pat. No. 4,727,064 discloses the production of pharmaceutical preparations containing cyclodextrin derivatives. Table 1 discloses complexes of estradiol, estriol and ethinyl estradiol-3-methyl ester (mestranol) with hydroxypropyl-β-cyclodextrin. For the estradiol, complexes with carboxamidomethyl-β-cyclodextrin and carboxymethyl-β-cyclodextrin are also described. This document is silent about an amorphous ethinyl estradiol-β-cyclodextrin complex.

Patent EP 1,353,700 discloses the production of a pharmaceutical product comprising ethinyl estradiol wherein the stability of the estrogen is improved over that of conventional products by means of complexing the estrogen with cyclodextrins. The complexes are obtained in crystalline form by co-precipitation of ethinyl estradiol and the β-cyclodextrin from a water-ethanol or a water-acetone solution. The processes in the co-precipitation method are relatively long and can promote solvent cyclodextrin cavity competition. Despite reproducing the same process, the amount of ethinyl estradiol bonded in the complexes formed varies from 90.1 to 98.7% and in most of the cases is below 97%.

Another disadvantage associated with the processes of the prior art is that the co-precipitation method to produce the complexes is relatively long (many hours or days for equilibration to take place) with a risk of decomposition of the active compound (hydrolysis). Large quantities of solvents have to be used. Additionally, the crystals obtained can also vary in particle size and shape and the poor control of the particle size distribution of the particles obtained makes it necessary to later micronize the product to assure its proper dissolution.

Thus, there is still need of new efficient processes for the preparation of ethinyl estradiol β-cyclodextrin complexes and pharmaceutical compositions and formulations comprising it.

The inventors have surprisingly found that when the ethinyl estradiol β-cyclodextrin complexes are produced by spray drying a cyclodextrin-estrogen complex with higher than 97% of ethinyl estradiol bonded in the complex is obtained. Furthermore, the complex is obtained in amorphous form.

BRIEF DESCRIPTION OF THE INVENTION

The present invention was made in view of the prior art described above, and the object of the present invention is to provide an ethinyl estradiol β-cyclodextrin complex having enhanced solubility and stability. The complex is a binary system between ethinyl estradiol and β-cyclodextrin.

To solve the problem, the present invention provides, in a first aspect, an ethinyl estradiol β-cyclodextrin complex obtainable in amorphous form.

The amorphous ethinyl estradiol β-cyclodextrin complex as defined herein is more soluble than other crystalline forms and it is chemically and physically stable. The amorphous ethinyl estradiol β-cyclodextrin complex has advantageous properties in the preparation of pharmaceutical compositions such as increased solubility, improved bioavailability, easy of chemical processing and/or easy of pharmaceutical formulation. The amorphous ethinyl estradiol β-cyclodextrin complex of this invention is highly compatible with active ingredients such as progestogens, folic acid and tetrahydrofolic acid derivatives. These properties allow for preparing dosage forms containing the amorphous ethinyl estradiol β-cyclodextrin complex according to the invention.

In another aspect, the amorphous ethinyl estradiol β-cyclodextrin complex of the present invention is obtainable by a process, which is capable of improving the complexation efficiency.

Surprisingly, the process is capable of complexing more than 97% of the ethinyl estradiol in the amorphous complex, preferably more than 98%.

Advantageously, the process is capable of obtaining the complex of the invention with a reduction of manufacture time, and without requiring the presence of particular polymorphs or excipients so that allow to save time and raw materials for its production.

Another aspect of the present invention is a pharmaceutical composition comprising the amorphous ethinyl estradiol β-cyclodextrin complex as defined herein, and a pharmaceutically acceptable excipient and/or auxiliary agent. The pharmaceutical acceptable excipient and/or auxiliary agent can be selected with regard to the intended route of administration and standard pharmaceutical practice.

The amorphous ethinyl estradiol β-cyclodextrin complex of the present invention can be formulated into conventional dosage forms.

Another aspect of the present invention is, therefore, a process for preparing a dosage form comprising the amorphous ethinyl estradiol β-cyclodextrin complex of the present invention. In this aspect, the process comprises the steps of mixing the amorphous ethinyl estradiol β-cyclodextrin complex of the invention with at least one pharmaceutically acceptable excipient and/or auxiliary agent and, then, processing the mixture to produce the dosage form. In an embodiment, the mixture is processed by filling it into capsules or compressing it to obtain tablets.

The amorphous ethinyl estradiol β-cyclodextrin complex of the invention can be used, alone or in combination with other active ingredients. The active ingredients can be selected from the group consisting of a progestogen, folic acid or a tetrahydrofolic acid derivative.

The amorphous ethinyl estradiol β-cyclodextrin complex can, therefore, be blended with other active ingredients, and at least one pharmaceutical acceptable excipient and/or auxiliary agent selected with regard to the intended route of administration.

Another aspect of the invention is a pharmaceutical composition comprising the amorphous ethinyl estradiol β-cyclodextrin complex of the invention for use as a medicament in Hormonal Substitutive Therapy (HRT).

Another aspect of the invention is a pharmaceutical composition comprising the amorphous ethinyl estradiol β-cyclodextrin complex of the invention for use as a contraceptive medicament.

BRIEF DESCRIPTION OF THE DRAWINGS

FIGS. 1.1 and 1.2 depict the XPRD patterns of the amorphous ethinyl estradiol β-cyclodextrin complex obtainable according to example 1 (FIG. 1.1) and obtainable according to example 2 (FIG. 1.2).

FIGS. 4.1 and 4.2 depict the integrated DSC curves of the amorphous ethinyl estradiol β-cyclodextrin complex obtainable according to example 1 (FIG. 4.1) and obtainable according to example 2 (FIG. 4.2).

DETAILED DESCRIPTION OF THE INVENTION

Figure 2:
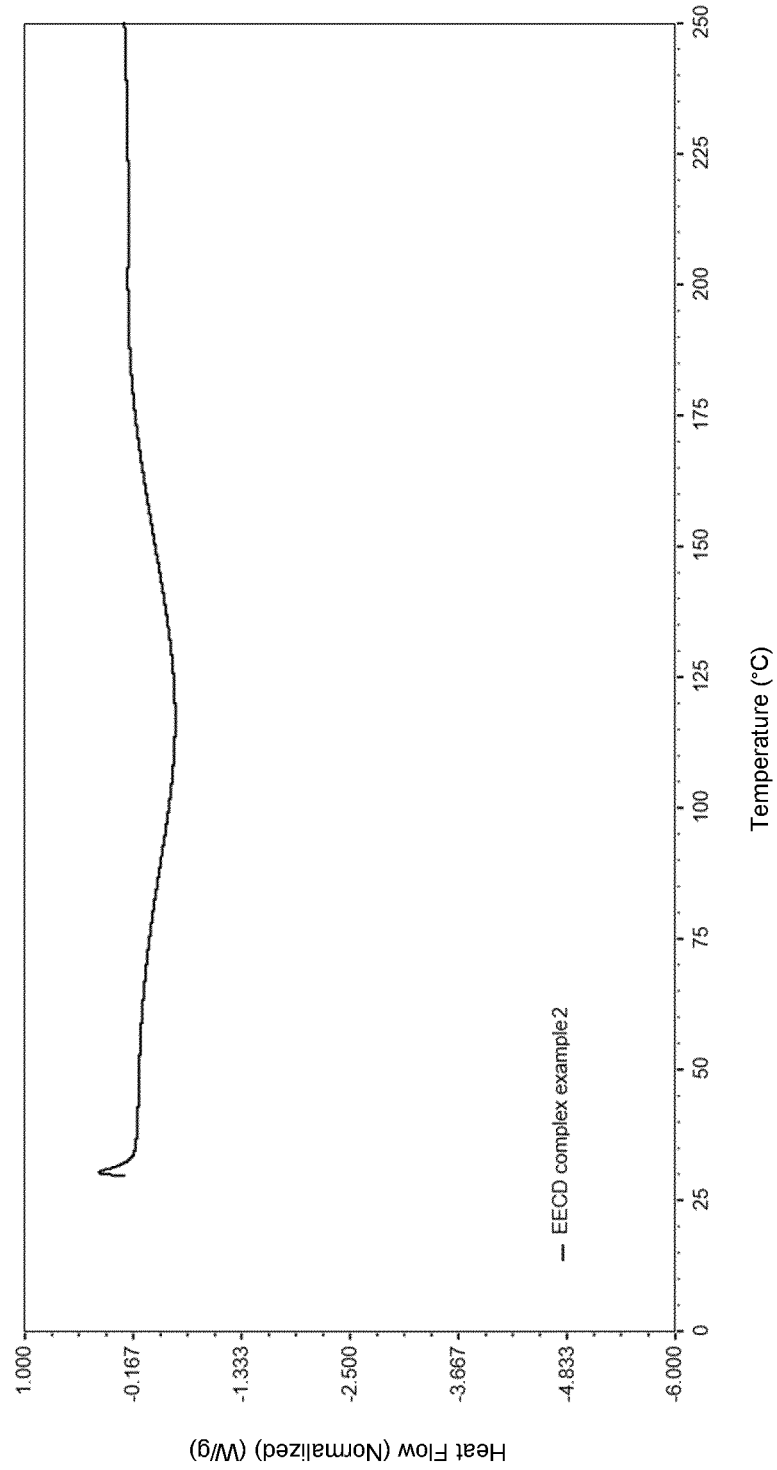
FIG. 2 depicts the DSC thermogram of the amorphous ethinyl estradiol β-cyclodextrin complex obtainable according to example 2.

All terms as used herein in this application, unless otherwise stated, shall be understood in their ordinary meaning as known in the art. Other more specific definitions for certain terms as used in the present application are set forth below and are intended to apply uniformly through-out the specification and claims unless otherwise expressly set out definition provides a broader definition.

Throughout the description and claims the word "comprise" and variations of the word, are not intended to exclude other technical features, additives, components, or steps. Furthermore, the word "comprise" encompasses the case of "consisting of". Additional objects, advantages and features of the invention will become apparent to those skilled in the art upon examination of the description or may be learned by practice of the invention. The following examples and drawings are provided by way of illustration, and they are not intended to be limiting of the present invention. Furthermore, the present invention covers all possible combinations of particular and preferred embodiments described herein.

The term "ethinyl estradiol-β-cyclodextrin complex" is intended to mean a complex between an ethinyl estradiol and a β-cyclodextrin, wherein the estrogen molecule is at least partially inserted into the cavity of a cyclodextrin molecule.

As used herein, the term "amorphous ethinyl estradiol-β-cyclodextrin complex" unless otherwise specified, is meant that the ethinyl estradiol-β-cyclodextrin complex is in a non-crystalline state.

According to one aspect, the present invention provides a process for preparing ethinyl estradiol-β-cyclodextrin complex, the process comprising:
 a) dissolving β-cyclodextrin in water, optionally with heating, to form a β-cyclodextrin solution;
 b) dissolving ethinyl estradiol in a solvent selected from the group consisting of water, a C1-C4 alcohol, a C2-C4 ketone, a C2-C6 ester or mixtures thereof, optionally with heating, to form a ethinyl estradiol solution;
 c) combining the β-cyclodextrin solution and the ethinyl estradiol solution to form a combined solution, optionally with heating; and
 d) removing the solvent by spray-drying thereby obtaining the ethinyl estradiol-β-cyclodextrin complex in amorphous form.

In preferred embodiments of the invention, the molar ratio between the ethinyl estradiol and the β-cyclodextrin is from about 1:1 to 1:5, preferably 1:2.

Spray-drying processes and spray-drying equipment are described generally in Perry's Chemical Engineers' Handbook, pages 20-54 to 20-57 (Sixth Edition 1984). More details on spray-drying processes and equipment are reviewed by Marshall, "Atomization and Spray-Drying," 50 Chem. Eng. Prog. Monogr. Series 2 (1954), and Masters, Spray Drying Handbook (Fourth Edition 1985).

Preferably, in step a), the aqueous solution or suspension obtained is heated between 30 to 40° C., more preferably, between 35 to 39° C. In the most preferred embodiment, the solution is heated at 37° C.

Preferably, in step b), the aqueous solution or suspension obtained is heated between 20 to 50° C., more preferably, between 21 to 35° C. In the most preferred embodiment, the solution is heated between to 25 to 30° C.

Preferably, in step c), heating is performed between 30 to 50° C., more preferably, between 35 to 45° C.

Suitable solvents used in step b) are selected from the group consisting of a C1-C4 alcohol, a C2-C4 ketone, a C2-C6 esters or mixtures thereof. Suitable solvents are selected but not limited to acetone, methyl ethyl ketone and methyl iso-butyl ketone; alcohols such as methanol, ethanol, n-propanol, iso-propanol, and butanol; esters such as ethyl acetate and propylacetate. Preferably, the solvent used is water, ethanol or mixtures thereof.

Typically, the solvent used in step b) is ethanol.

Preferably, the solvent used in steps a) and/or b) is a mixture of water and ethanol in an amount water:ethanol of 99:1.

In the spray-drying step d), the obtained particles have been found to be amorphous.

As used herein, the term amorphous means that the amorphous form includes at most 20 percent, preferably at most 10 percent, more preferably at most 5 percent, even more preferably at most 2 percent and most preferably at most 1 percent by weight of any crystalline form. The amount of ethinyl estradiol in the amorphous form can be measured by X-ray diffraction and Differential Scanning Calorimetry (DSC).

Present inventors have found that the solubility of ethinyl estradiol is substantially increased with the amorphous complex of the invention. Advantageously, the particulate amorphous complex obtained in the spray-drying step is rapidly dissolved, meaning that it should release at least 50% of its content in 5 minutes and at least 80% of its content.

Mean particle size (D50) of the particles obtained according to the process of the invention is typically lower than 50 micrometers, preferably lower than 30 micrometers, more preferably lower than 20 micrometers, even more preferably lower than 10 micrometers. Further, D90 of the particles obtained according to the process of the invention is typically lower than 20 micrometers, preferably lower than 12 micrometers.

The invention is directed to an amorphous ethinyl estradiol-β-cyclodextrin complex.

In another aspect, the invention provides an amorphous ethinyl estradiol f-cyclodextrin complex, which is obtainable by the process defined above.

Surprisingly, the obtainable amorphous ethinyl estradiol f-cyclodextrin complex has more than 97% of the ethinyl estradiol bonded in the amorphous complex, preferably more than 98%.

In another aspect, the invention provides a dosage form. The dosage form comprises:
an amorphous ethinyl estradiol-β-cyclodextrin complex as described herein, and
at least one or more pharmaceutically acceptable excipient and/or auxiliary agent.

Dosage forms may include those for oral administration, buccal administration, vaginal administration, rectal administration, topical or mucosal delivery, implants for subcutaneous delivery or other implanted drug delivery systems. Suitable oral dosage forms of the present invention include, but are not limited to granules, pellets, multiparticles, tablets, caplets, capsules (soft and hard), lozenges, sachets, dispensable powders and the like. In a preferred embodiment, the dosage form of the present invention is a tablet.

The amorphous ethinyl estradiol β-cyclodextrin complex can be present in the dosage form in an amount of 0.01% to 10% by weight of the of the total weight of the dosage form, preferably from about 0.01 to 5% by weight, more preferably from 0.01 to 2% by weight of the total weight of the formulation.

The amount of ethinyl estradiol in a dosage form is those normally used in hormonal replacement therapy (HRT) or contraceptives, for example from 100 to 10 micrograms, preferably from 50 to 10 micrograms.

The unit solid dosage form of the invention may, if desired, include a further active ingredient. The active ingredients can be selected from the group consisting of a progestogen, folic acid or a tetrahydrofolic acid derivative.

In a preferred embodiment, said further active ingredient is a progestogen.

Suitable progestogens include, but are not limited to drospirenone, levonorgestrel, progesterone, dydrogesterone, medrogestone, medroxyprogesterone acetate, megestrol, chlormadinone, cyproterone, nomegestrol, promegestone, trimegestone, norethisterone acetate, norgestimate, desogestrel, 3-ketodesogestrel, norgestimate, gestodene, tibolone, cyproterone acetate, dienogest, ethynodiol diacetate, norethynodrel, allylestrenol, lynestrenol, quingestanol acetate, norgestrienone, dimethisterone and ethisterone. In a preferred embodiment, the progestogen is drospirenone.

Progestogen may be present in an amount from about 0.1% to 60% by weight, preferably from about 0.2% to 40% by weight, more preferably from 0.3% to 30% by weight of the total weight of the dosage form.

The amounts of progestogen are those normally used in contraceptives or in a hormonal replacement hormonal therapy (HRT), for example: 0.5-5 mg of drospirenone, 30-250 mg levonorgestrel, 180-250 mg norgestimate, 2-3 mg dienogest, 0.5-1 mg norethisterone (norethindrone) acetate, 20-150 g desogestrel, 2-4 mg tibolone. Preferred amounts of drospirenone are from 1 to 4 mg, preferably from 2 to 3 mg.

In another preferred embodiment, said further active ingredient is folic acid or one or more tetrahydrofolate components selected from the group consisting of (6S)-tetrahydrofolic acid, 5-methyl-(6S)-tetrahydrofolic acid, 5-formyl-(6S)-tetrahydrofolic acid, 10-formyl-(6R)-tetrahydrofolic acid, 5,10-methylene-(6R)-tetrahydrofolic acid, 5,10-methenyl-(6R)-tetrahydrofolic acid, 5-formimino-(6S)-tetrahydrofolic acid, and pharmaceutically acceptable salts thereof.

Folic acid and tetrahydrofolate compounds may be present in an amount from about 0.1% to 60% by weight, preferably from about 0.2% to 40% by weight, more preferably from 0.3% to 30% by weight of the total weight of the composition.

Preferably, the dosage form according to the invention comprises 5-methyl-(6S)-tetrahydrofolic acid. More preferably, the dosage form according to the invention comprises the calcium salt of 5-methyl-(6S)-tetrahydrofolic acid. Crystalline forms of the calcium salt of 5-methyl-(6S)-tetrahydrofolic acid disclosed in application EP 1044975 A and the stabilized amorphous form of the calcium salt of 5-methyl-(6S)-tetrahydrofolic acid disclosed on patent application WO 2014/146975 A1 are particularly preferred.

Typically, the amount used of calcium 5-methyl-(6S)-tetrahydrofolate in the dosage form of the invention is between 0.1 and 10 mg, preferably 0.2 to 1 mg, particularly preferred 0,451 mg. In a most preferred aspect of the invention, the unit dosage form of the invention comprises 3 mg of drospirenone and 20 to 30 μg of ethinyl estradiol and 0.1 mg to 1 mg of calcium 5-methyl-(6S)-tetrahydrofolate.

The dosage form of the invention may include at least one or more further auxiliary agents, which may be added during the appropriate step so as to afford the appropriate mechanical and release properties. All such auxiliary agents must be compatible with the other ingredients of the dosage form and not injurious to the human being.

The auxiliary agent may be selected from the group consisting of diluents, binders, lubricants, and disintegrating, antiadherent, colouring, sweetening, flavouring agents, and/or mixtures thereof.

Suitably, the dosage form according to the invention comprises a diluent. Suitable diluents include corn starch, microcrystalline cellulose, powdered cellulose, silicified cellulose, lactose monohydrate, anhydrous lactose, mannitol, sorbitol, sucrose, fructose, dextrose, and/or mixtures thereof. Preferably, lactose monohydrate and microcrystalline cellulose are used.

Diluents may be presents in an amount from about 20% to about 95% by weight, preferably from 35% to 90% by weight, and more preferably form 30 to 85% by weight of the total weight of the composition.

Suitably, the dosage form according to the invention comprises a binder. The binding agent can be selected from the group consisting of hydroxypropyl cellulose, hydroxypropyl methyl cellulose, hydroxyethyl cellulose, methylcellulose, polyvinylpyrrolidone, sodium carboxymethyl cellulose, calcium carboxymethyl cellulose, and/or mixtures thereof.

Diluents may be presents in an amount from about 20% to about 95% by weight, preferably from 35% to 90% by weight, and more preferably from 30 to 85% by weight of the total weight of the composition.

The dosage form according to the invention can also comprise a disintegration agent. Disintegrating agents may be selected from the group consisting of low-substituted hydroxypropyl cellulose, sodium carboxymethyl cellulose, calcium carboxymethyl cellulose, crospovidone, sodium croscarmellose, and/or mixtures thereof. Preferably sodium croscarmellose is used.

Disintegrating agents may be present in an amount from about 10% to about 50% by weight, preferably from about 15% to about 45% by weight, and more preferably from 20% to 40% by weight of the total weight of the composition.

Lubricants and antiadherent agents are excipients that reduce interparticular friction and prevent adhesion of drug particles and improve fluidity of granular or pulverulent compositions.

Lubricants may be selected from the group consisting of talc, alkaline earth salts of stearic acid, specially magnesium and calcium stearate, stearic acid, glycerin palmitostearate, stearyl fumarate, and/or mixtures thereof.

The lubricant may be present in an amount from about 0% to 5% by weight, preferably from about 0% to about 3% based on the total weight of the composition.

The antiadherent agent may be present in an amount from about 0% to 5% by weight, preferably from about 0% to about 3% based on the total weight of the composition.

The dosage form according to the invention can also comprise a surfactant. Suitable surfactant agents may be selected from the group consisting of ionic surfactants, such as Sodium Lauryl Sulfate, Phospholipids, Glycerol Monooleate, Docusate sodium, or non-ionic surfactant, such as polisorbate 80, Polyoxyethylene Sorbitan Fatty Acid Esters, Polyoxyethylene Stearates, poloxamers, poloxamines, Polyoxyethylene Alkyl Ethers.

The surfactant agent may be present in an amount from about 0% to 10% by weight, preferably from about 0% to about 5% based on the total weight of the composition.

The dosage form of the invention may also contain sweetening and flavouring agents in order to provide acceptable organoleptic properties (flavour and taste) for patients. Suitable sweetening agents include sodium saccharin, aspartame, mannitol, xylitol, sucrose, sorbitol and ammonium glycyrrhizinate. Suitable flavouring agents include fruit and plant flavours, for example orange, anise, mint, etc. Suitable colouring agents, which may be incorporated into the dosage form of the invention, may be selected from those approved for oral use.

The dosage form may be coated using conventional methods known to a person skilled in the art, as those described in Remington: The Science and Practice of Pharmacy, $20^{th}$ 10 Edition, Philadelphia, Lippincott, Williams & Wilkins, 2000 [ISBN 0 683 306472]. Among the film-forming agents which are used for coating the tablets, polyvinylpyrrolidone, hydroxypropyl methyl cellulose, hydroxypropyl cellulose, methyl cellulose, ethyl cellulose, hypromelose, solid polyethylenglycol, and polyvinyl alcohol may be included.

Information on the characteristics of auxiliary agents is described in reference handbooks available to those skilled in the art, for example in Handbook of Pharmaceutical Excipients, 4th Edition, London, Pharmaceutical Press, 2003 [ISBN 0 85369 472 9] wherein, in addition, the trade names of commercially available auxiliary agents are included.

According to yet another aspect, the invention provides a process for preparing a dosage form, the process comprising:
  i) preparing an amorphous ethinyl estradiol β-cyclodextrin complex in particulate form;
  ii) mixing the particles of step i) with at least one pharmaceutically acceptable excipient and/or auxiliary agent, and
  iii) optionally, mixing either the particles of step i) or the mixture of step ii) with a further active ingredient.

The dosage form according to the invention can be prepared from the blend obtained in steps ii) or iii) by: filing a capsule with the blend; direct compression of the blend; or wet or dry granulation of the blend to form a granulate for incorporation into the dosage form.

In a preferred embodiment, step i) includes above steps a) to d), and then above steps ii) and iii).

In the preferred embodiment, the process for preparing a dosage form comprises:
  a) dissolving the β-cyclodextrin in water, optionally with heating, to form a β-cyclodextrin solution;
  b) dissolving the ethinyl estradiol in a solvent selected from the group consisting of water, a C1-C4 alcohol, a C2-C4 ketone, a C2-C6 ester or mixtures thereof, optionally with heating, to form a ethinyl estradiol solution;
  c) combining the β-cyclodextrin solution and the ethinyl estradiol solution to form a combined solution;
  d) removing the solvent by spray-drying thereby obtaining amorphous ethinyl estradiol β-cyclodextrin complex in particulate form;
  e) mixing the particles of step d) with at least one pharmaceutically acceptable excipient, and
  f) optionally, mixing either the particles of step d) or the mixture of step e) with a further active ingredient.

The active ingredient has the same meaning as stated above.

In still another aspect, the invention is directed to the use of the dosage form of the invention for the production of a pharmaceutical composition suitable for the treatment of menopausal symptoms, or hormonal replacement therapy (HRT).

The dosage form of the invention can be used as contraceptive in conjunction with a contraceptive regimen. As used herein, a contraceptive regimen refers to any of a monophasic, biphasic, multiphasic, extended or flexible contraceptive regimens. The invention will be further illustrated by the following examples.

EXAMPLES

A. Physical Mixture

Physical mixture (PM) was prepared by blending EE and βCD (1:2 molar ratio). PM was stored in a glass bottle.

B. Ethinyl Estradiol β-Cyclodextrin Complexes

β-cyclodextrin used to manufacture complexes of examples 1 and 2 was Kleptose® 7%-βCD (Roquette—France).

Quantities of EE and βCD (1:2 molar ratio) to obtain a theoretical amount of complex of 10 g were dissolved in ethanol (1%) and purified water (99%) for a total amount of 2.875 mL at 38±2° C. and mixed. The mixture was agitated during approximately 1 h until a clear solution was obtained. The final clear solution was maintained at 38±2° C. and was spray-dried in a Mini Spray Dryer B-290, under the following conditions: inlet temperature 150° C., outlet temperature 77° C., flow rate of the solution 370 mL/h, airflow rate 35 m³/h, and atomizing air pressure 0.5 bar.

TABLE 1

|  | EEβCD-Example 1 | EEβCD-Example 2 |
|---|---|---|
| Complex stoichiometry | (1:2) | (1:2) |
| BETADEX Concentration (mM) | 4.4 | 4.4 |
| Mix. Temperature (° C.) | 38 ± 2 | 38 ± 2 |
| Yield (%) | 55.0 | 52.8 |
| Water content (%) | 8.1 | 7.6 |
| EE Assay (11.55%) | 11.4% (98.7%) | 11.6 (100.4%) |

The amount of EE in each of the complexes (EEβCD) was determined according to the final weight obtained of the solid complex. The EE assay was determined using the solid complex (100 mg of complex) containing 11.55 mg of the drug (Table 1), that is, a complex containing 11.55% of EE, present an assay of 100%. The EE concentration after suitable dilution in an adequate solvent (100 ml) was determined at 220 nm by HPLC.

1. Differential Scanning Calorimetry (DSC)

DSC measurements of the pure materials and binary systems were carried out. The thermal behavior was studied by heating the samples (2 mg) in a perforated aluminum pan from 30° C. to 250° C., at a rate of 10° C./min, and under a nitrogen flow of 20 cm³/min. An empty pan should be sealed (perforated) and used as a reference.

Figure 3:
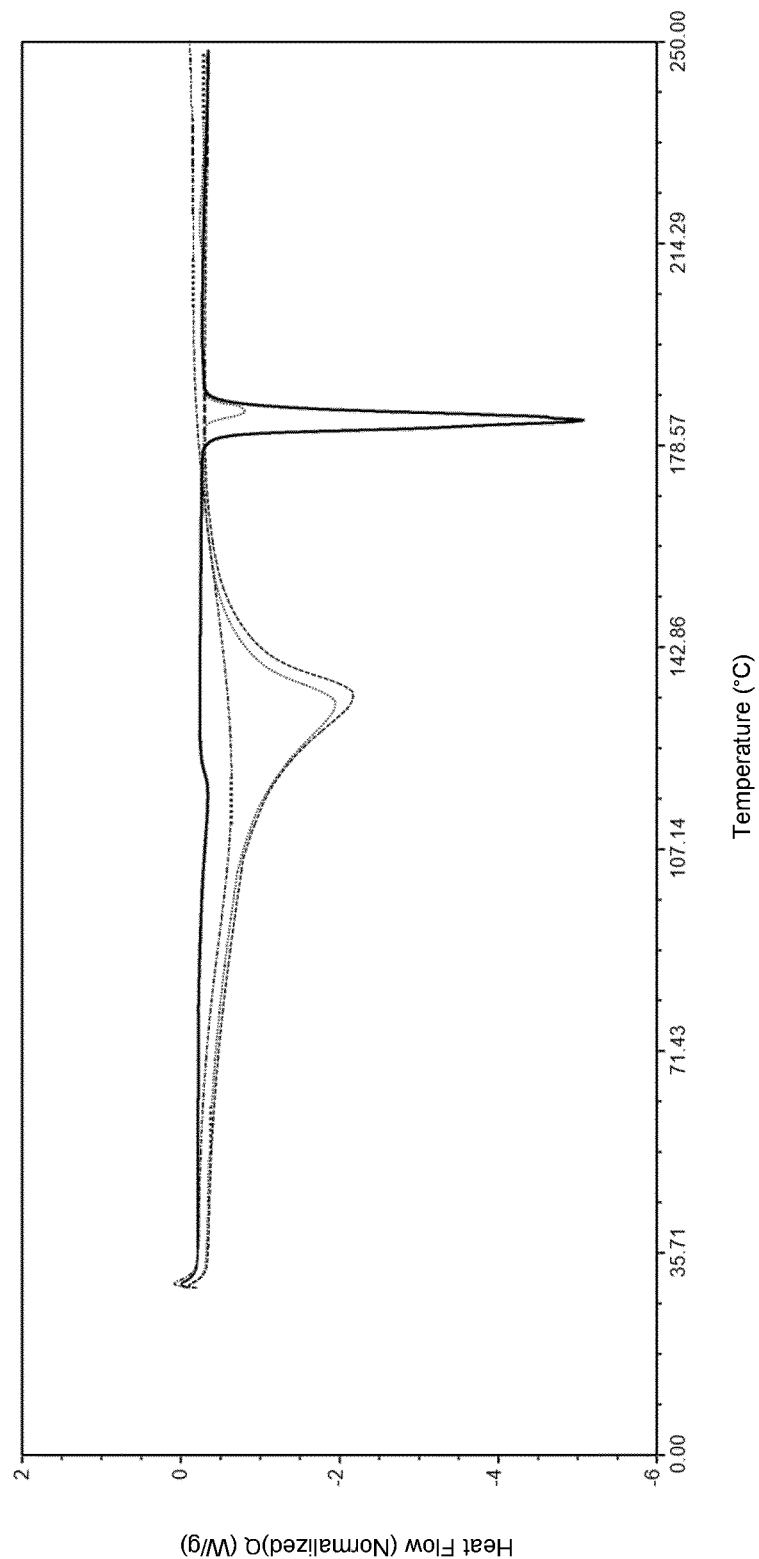
FIG. 3 depicts the DSC thermograms of the amorphous ethinyl estradiol β-cyclodextrin complex obtainable according to example 2 compared with the individual thermograms of ethinyl estradiol and the physical mixture of ethinyl estradiol with s-cyclodextrin.

In order to perform DSC, the guest must have a melting or boiling temperature below 300° C., the temperature at which CDs decomposes. In DSC analysis, no energy absorption is observed at the melting temperature of the guest when the guest is complexed. Thermograms of the complex obtained in example 2 compared with the individual thermograms of ethinyl estradiol and the physical mixture is presented in FIG. 3, wherein (-) refers to etinil estradiol; (- - -) refers to beta-ciclodextrina; ( . . . ) refers to a physical mixture EE with BCD; and (- . - . -) refers to EE-BDC\Example 2. FIG. 2 shows the thermogram of the complex obtained in example 2. The thermal curve of EE shows an endothermic peak at 183.05° C., corresponding to the melting point of the drug 180-186° C. The DSC curve of βCD exhibits a typical broad effect between 30 and 150° C. associated with crystal water losses. The disappearance of the EE and βCD melting point in the complexed systems 1:2 shows the formation of a true inclusion complex indicating a more stable and strong interaction between drug and CD in these systems.

FIGS. 4.1 and 4.2 show integrated DSC curves of the complexes obtained in examples 1 and 2. In FIG. 4.1, the numeral reference 1: indicates: Integral 90.57 mJ, Normalized 36.08 Jg⁻¹, Onset 312.61° C., Peak 336.77° C.; the numeral reference 2: indicates Integral −163.43 mJ, Normalized −65.11 Jg⁻¹, Onset 302.88° C., Peak 312.55° C.; the numeral reference 3: indicates: Integral −517.18 mJ, Normalized −206.05 Jg⁻¹, Onset 39.17° C., Peak 93.27° C. In FIG. 4.2, the numeral reference 1 indicates: Integral 154.65 mJ, Normalized 49.41 Jg⁻¹, Onset 323.47° C., Peak 335.76° C.; the numeral reference 2 indicates: Integral −208.93 mJ, Normalized −66.75 Jg⁻¹, Onset 302.17° C., Peak 313.01° C.; the numeral reference 3 indicates: Integral −658.23 mJ, Normalized −210.30 Jg⁻¹, Onset 42.37° C., Peak 97.91° C. Both DSC curves show similar thermal events. The first one is a broad endothermic peak, approximately between room temperature and nearly 160° C., probably caused by dehydration of the products. This hypothesis is also supported by the fact that this thermal event takes place at a similar temperature range that the loss of weight seen in the TGA curves (see thermogravimetric analysis section below).

Then, the other two thermal events are an irregular broad endothermic peak, approximately between 280 and 320° C., followed by a broad exothermic peak, with onset values approximately between 312.6 and 323.5° C. These both thermal events seem to be the sum of some individual processes.

2. X-Ray Powder Diffraction

The diffraction measurements of ethinyl estradiol ethinyl estradiol β-cyclodextrin complexes obtained in examples 1 and 2 (FIGS. 1.1 and 1.2) was performed at ambient conditions (22-24° C./28-33% RH) on a PANalytical X'Pert PRO θ-θ diffractometer of 240 mm of radius in reflection geometry, equipped with Cu Kα radiation and a PiXcel detector, operated at 45 kV and 40 mA. The sample was mounted on a back-loaded steel sample holder (16 mm diameter) and allowed to spin at 0.25 rev/s dung the data collection. The measurement angular range was 3.0-40.0° (2θ) with a step size of 0.013°. The scanning speed was 0.00513°/s (652.80 s/step). The shoulder in the 3-4° 2θ range seen in the diffractograms is due to instrumental reasons and is not caused by any crystalline contents.

The general profile of the diffractogram is typical of a predominantly amorphous content for each sample. No signs of the EE API or βCD signals are detected in the measured diffractogram. One broad peak seen around 15.6° in the diffractogram nearly coincide with the position of one prominent peak of EE API diffractogram. However, the lack of other signals in the same sample diffractogram that could be related to the other intense peaks from the EE API diffractogram indicates that this peak is not caused by the presence of crystalline ethinyl estradiol.

3. IR

Figure 5:
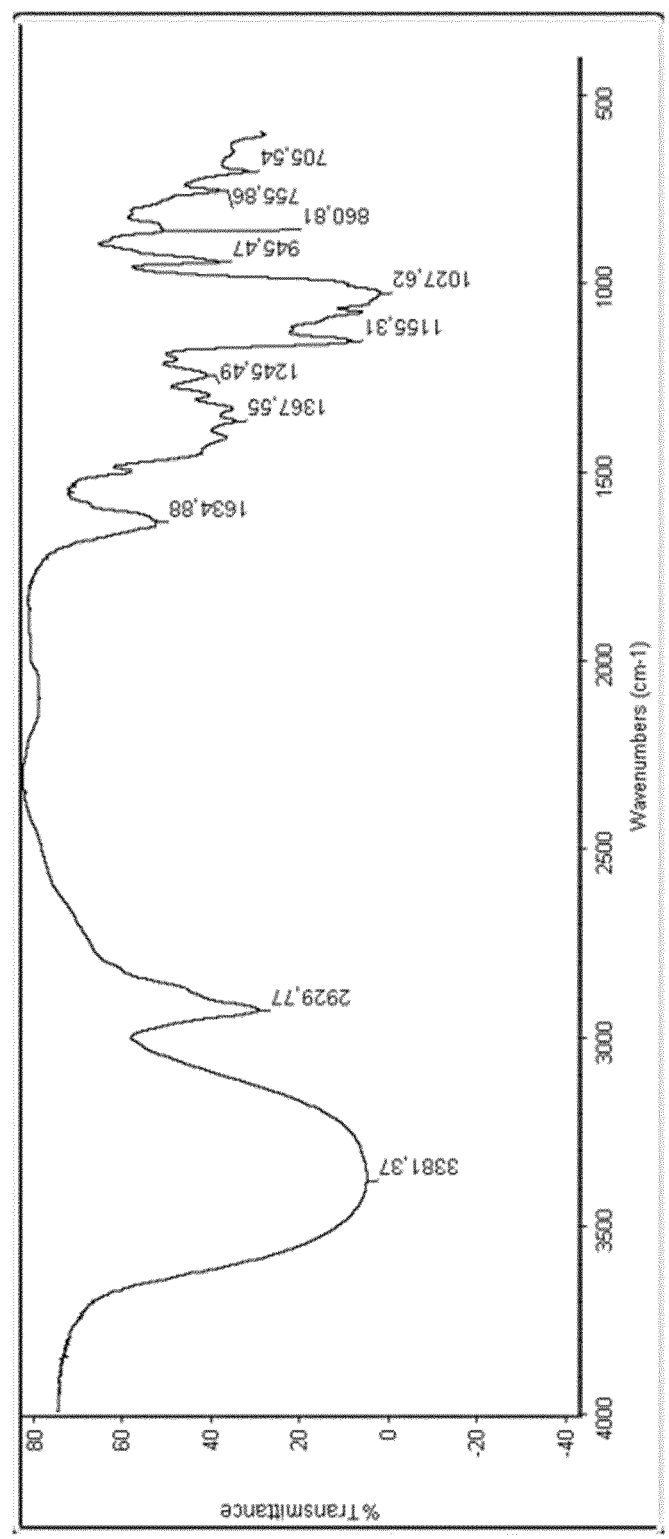
FIG. 5 depicts the infrared spectrum of EEβCD complex obtainable according to example 1.

Generally, when a complex is formed, there are shifts in absorbance bands to a lower frequency, increases or decreases in intensity, and broadening of bands involved in the formation of hydrogen bonds, comparing with the bands of the raw materials. When IR is used to characterize CD complexes, information about particular bands can be used to determine if a complex has been formed. CDs naturally hold energy-rich water molecule in their cavities and upon complexation in solution state, these water molecules are released from the cavity and replaced by a molecule that is less polar. IR studies can be used to observe a change in the intensity or shift of the water band as confirmation that an inclusion complex has been formed. FIG. 5 shows the Infrared spectrum of EEβCD complex (1:2). The characteristic band of the βCD at 1.021 cm$^{-1}$ is present in SD system at 1.027.62 cm$^{-1}$. Even in the spray-drying (SD) systems showed drug bands, the EE bands are not detectable. The FTIR spectrum of SD products shows the strong reduction or the complete disappearance of the characteristic EE bands, indicative of strong drug-CD interactions and inclusion complexation of the drug, thus substantially confirming the results previously obtained by DSC, SEM, and Raman. The changes observed in the FTIR spectra of the SD sample, such as shift of peaks or their reduction in intensity up to almost complete disappearance, depended on their preparation's conditions.

4. SEM

Figure 6:
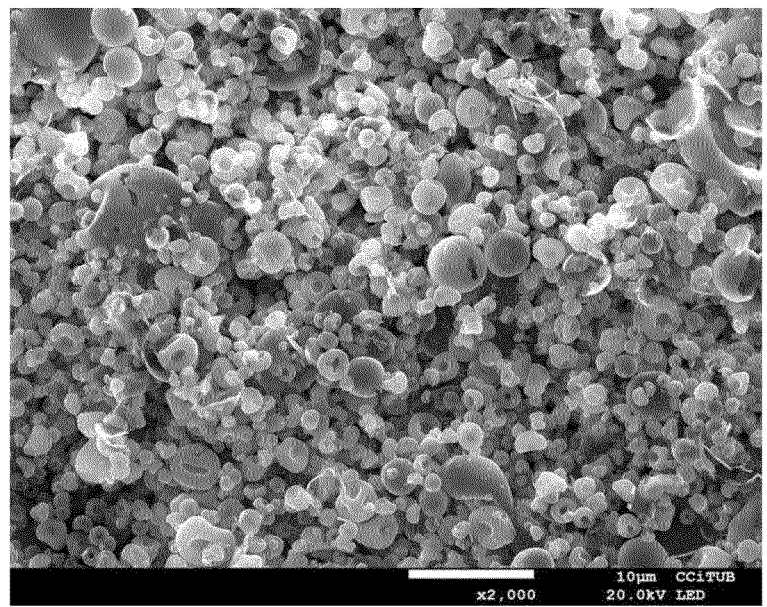
FIGS. 6 and 7 depict the SEM photographs of the inclusion amorphous ethinyl estradiol β-cyclodextrin complex obtainable according to examples 1 and 2, respectively.
Figure 7:
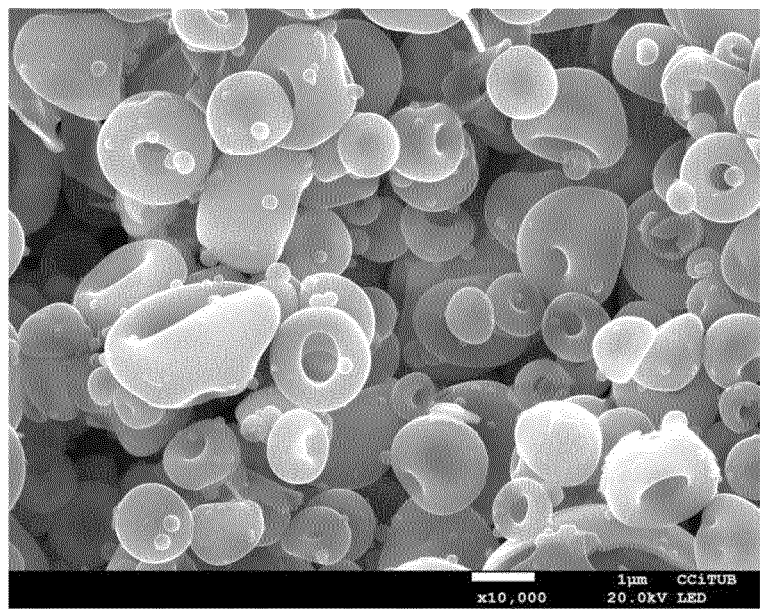

SEM is a qualitative method used to study the structural aspect of raw materials and the products obtained by complexation with CDs. FIGS. 6 and 7 illustrate the SEM photographs of the inclusion complexes obtained in examples 1 and 2. It is observed the presence of amorphous and homogeneous aggregates of spherical particles in a unique form, a particular aspect characteristic of this type of system.

Prior to analysis, the samples were mounted on a bioadhesive tape and coated with carbon to enhance the electrical conductivity using an Emitech K950X evaporator. Micrographs were examined with a J-7100 Field Emission (Jeol) Electron Microscope under high vacuum conditions using a secondary electron detector at magnifications of 2000× and 10000×.

5. Stability

To determine the drug complex stability, a stability study was carried out for 3 months according to the ICH guidelines. The complex obtained in example 1 and 2 were withdrawn according to the interval time presented in Table 2 below and evaluated for appearance, water content and assay.

TABLE 2

| Material/Preparation methods | Conditions | Time | | |
|---|---|---|---|---|
| | | 15 days | 1 Month | 3 Months |
| Spray-dried complex | 25° C./60% HR | | X | X |
| | 40° C./75% HR | X | X | X |
| | 60° C./75% HR | X | X | |

Table 2.1 shows the results of stability to EEβCD of example 1

As can be seen in the above table, ethinyl estradiol content of the complex remain constant after 3 months at all the conditions tested.

The invention claimed is:

1. A process for preparing ethinyl estradiol-β-cyclodextrin complex, wherein the process comprising:
   a) dissolving β-cyclodextrin in water to form a β-cyclodextrin solution;
   b) dissolving ethinyl estradiol in a solvent selected from the group consisting of water, a C1-C4 alcohol, a C2-C4 ketone, a C2-C6 esters or mixtures thereof to form a ethinyl estradiol solution;
   c) combining the β-cyclodextrin solution and the ethinyl estradiol solution to form a combined solution; and
   d) removing the solvent by spray-drying to obtain the ethinyl estradiol-β-cyclodextrin complex in amorphous form.

2. The process according to claim 1, wherein the molar ratio between the ethinyl estradiol and the β-cyclodextrin is from about 1:1 to 1:5, preferably 1:2.

3. The process according to claim 1, wherein in step b) the solvent is selected from acetone, methyl ethyl ketone, methyl iso-butyl ketone, methanol, ethanol, n-propanol, iso-propanol, butanol, ethyl acetate, propylacetate or a mixture of water with ethanol.

4. An amorphous ethinyl estradiol-β-cyclodextrin complex, wherein the amorphous ethinyl estradiol-β-cyclodextrin complex comprises more than 97% of the ethinyl estradiol bonded to the amorphous complex.

5. An amorphous ethinyl estradiol-β-cyclodextrin complex obtained by a method comprising:
   a) dissolving β-cyclodextrin in water to form a β-cyclodextrin solution;
   b) dissolving ethinyl estradiol in a solvent selected from the group consisting of water, a C1-C4 alcohol, a C2-C4 ketone, a C2-C6 esters or mixtures thereof to form a ethinyl estradiol solution;
   c) combining the β-cyclodextrin solution and the ethinyl estradiol solution to form a combined solution; and
   d) removing the solvent by spray-drying to obtain the ethinyl estradiol-β-cyclodextrin complex in amorphous form,
   wherein the amorphous ethinyl estradiol-β-cyclodextrin complex comprises more than 97% of the ethinyl estradiol bonded to the amorphous complex.

6. A dosage form comprising the amorphous ethinyl estradiol-β-cyclodextrin complex of claim 5 as an active ingredient and at least one pharmaceutically acceptable excipient and/or auxiliary agent.

| | | | Condition | | | | |
|---|---|---|---|---|---|---|---|
| | | | 25° C. 60% HR | | 40° C. 75% HR | | 60° C. 75% HR |
| TESTS | Acceptance criteria | T0 | 1 month | 3 months | 1 month | 3 months | 15 days | 1 month |
| BETADEX ASSAY (%) | 78.5-98.5% | 91.6% | 92.9% | 92.8% | 92.6% | 93.0% | 90.1% | 93.0% |
| ETHINYL ESTRADIOL ASSAY (%) | 9.5-13.5% | 11.4% | 11.3% | 11.4 | 10.9% | 11.5 | 11.5% | 11.5 |
| WATERT CONTENT (%) | ≤14.0% | 8.1% | 8.7% | 7.8% | 8.9% | 8.6% | 8.0% | 8.6% |
| TOTAL IMPURITIES | ≤2.5% | 0.61% | 0.39% | 0.95% | 0.18% | 1.04% | 0.5% | 1.26% |

7. The dosage form according to claim 6, wherein the dosage form further comprises a progestogen, folic acid, or a tetrahydrofolic acid derivative as a further active ingredient.

8. The dosage form according to claim 7, wherein the progestogen is selected from levonorgestrel, progesterone, dydrogesterone, medrogestone, medroxyprogesterone acetate, megestrol, chlormadinone, cyproterone, nomegestrol, promegestone, trimegestone, norethisterone acetate, norgestimate, desogestrel, 3-ketodesogestrel, norgestimate, gestodene, tibolone, cyproterone acetate, dienogest, ethynodiol diacetate, norethynodrel, allylestrenol, lynestrenol, quingestanol acetate, norgestrienone, dimethisterone and ethisterone.

9. The dosage form according to claim 7, wherein the folic acid or the tetrahydrofolic acid derivative as a further active ingredient, wherein the folic acid or the tetrahydrofolic acid derivative is selected from the group consisting of (6S)-tetrahydrofolic acid, 5-methyl-(6S)-tetrahydrofolic acid, 5-formyl-(6S)-tetrahydrofolic acid, 10-formyl-(6R)-tetrahydrofolic acid, 5,10-methylene-(6R)-tetrahydrofolic acid, 5,10-methenyl-(6R)-tetrahydrofolic acid, 5-formimino-(6S)-tetrahydrofolic acid, and pharmaceutically acceptable salts thereof.

10. A process for preparing the dosage form of claim 6, the process comprising:

(i) preparing an amorphous ethinyl estradiol β-cyclodextrin complex in particulate form; and (ii) mixing the particles of step i) with at least one pharmaceutically acceptable excipient, and/or auxiliary agent.

11. The process of claim 10, wherein the pharmaceutically acceptable excipient, and/or auxiliary agent is selected from the group consisting of diluents, binders, lubricants, and disintegrating, antiadherent, colouring, sweetening, flavouring agents, and/or mixtures thereof.

12. The process of claim 1, further comprising heating the β-cyclodextrin solution formed in the step (a).

13. The process of claim 1, further comprising heating the ethinyl estradiol solution formed in the step (b).

14. The process of claim 1, further comprising heating the combined solution formed in the step (c).

15. The process of claim 10, wherein the process further comprising mixing either the amorphous ethinyl estradiol β-cyclodextrin complex in particulate form of step (i) or the mixture of step (ii) with a further active ingredient.

16. The process according to claim 14, wherein heating in step c) is performed between 30 and 50° C., preferably between 35 and 45° C.

17. A method for hormonal treating of Hormonal Substitutive Therapy (HRT), the method comprising administering to a subject in need thereof a composition comprising an effective amount of the amorphous ethinyl estradiol β-cyclodextrin complex of claim 4 and one or more pharmaceutically acceptable excipients.

18. The method of claim 17, wherein the hormonal treating is contraceptive.

* * * * *